(12) United States Patent
Ampulski et al.

(10) Patent No.: US 8,961,628 B2
(45) Date of Patent: Feb. 24, 2015

(54) PRETREATMENT OF BIOMASS USING STEAM EXPLOSION METHODS

(75) Inventors: Robert S. Ampulski, Fairfield, OH (US); John T. Turner, West Chester, OH (US); Wayne W. Simmons, Longmont, CO (US)

(73) Assignee: Sundrop Fuels, Inc., Longmont, CO (US)

( * ) Notice: Subject to any disclaimer, the term of this patent is extended or adjusted under 35 U.S.C. 154(b) by 0 days.

(21) Appl. No.: 13/531,318

(22) Filed: Jun. 22, 2012

(65) Prior Publication Data
US 2013/0341569 A1    Dec. 26, 2013

(51) Int. Cl.
*B01J 7/00*    (2006.01)

(52) U.S. Cl.
USPC .......................................................... 48/61

(58) Field of Classification Search
None
See application file for complete search history.

(56) References Cited

U.S. PATENT DOCUMENTS

| | | | |
|---|---|---|---|
| 5,196,460 A | 3/1993 | Lora et al. |
| 5,747,320 A | 5/1998 | Saha et al. |
| 5,769,934 A | 6/1998 | Ha et al. |
| 5,882,905 A | 3/1999 | Saha et al. |
| 6,172,204 B1 | 1/2001 | Sarkanen et al. |
| 6,555,350 B2 | 4/2003 | Ahring et al. |
| 6,660,506 B2 | 12/2003 | Nguyen et al. |
| 6,899,791 B2 | 5/2005 | Sabourin |
| 7,109,005 B2 | 9/2006 | Eroma et al. |
| 7,300,540 B2 | 11/2007 | Sabourin et al. |
| 7,625,728 B2 | 12/2009 | Eroma et al. |
| 7,713,381 B2 | 5/2010 | Sabourin et al. |
| 7,846,294 B2 | 12/2010 | Sabourin et al. |
| 7,919,070 B2 | 4/2011 | Stites et al. |
| 8,003,352 B2 | 8/2011 | Foody et al. |
| 8,028,945 B2 | 10/2011 | Gingras |
| 8,057,639 B2 | 11/2011 | Pschorn et al. |
| 8,157,195 B2 | 4/2012 | Gingras |
| 8,187,849 B2 | 5/2012 | Larsen |
| 8,192,854 B2 | 6/2012 | Borole |
| 2002/0159929 A1 | 10/2002 | Kaneko et al. |
| 2008/0022595 A1 | 1/2008 | Lemaire et al. |
| 2009/0221814 A1 | 9/2009 | Pschorn et al. |
| 2009/0286295 A1 | 11/2009 | Medoff et al. |
| 2010/0137459 A1 | 6/2010 | Stites et al. |

(Continued)

FOREIGN PATENT DOCUMENTS

WO    WO 2011/159154 A1    12/2011
WO    WO 2013/191897    12/2013

OTHER PUBLICATIONS

U.S. Appl. No. 61/119,062, filed Dec. 2, 2008, Stites.

(Continued)

*Primary Examiner* — Imran Akram
(74) *Attorney, Agent, or Firm* — Rutan & Tucker, LLP

(57) ABSTRACT

An integrated plant that includes a steam explosion process unit and biomass gasifier to generate syngas from biomass. A steam explosion process unit applies a combination of heat, pressure, and moisture to the biomass to make the biomass into a moist fine particle form. The steam explosion process unit applies steam with a high pressure to heat and pressurize any gases and fluids present inside the biomass to internally blow apart the bulk structure of the biomass via a rapid depressurization of the biomass with the increased moisture content. Those produced moist fine particles of biomass are subsequently fed to a feed section of the biomass gasifier, which reacts the biomass particles in a rapid biomass gasification reaction to produce syngas components.

12 Claims, 10 Drawing Sheets

(56) References Cited

U.S. PATENT DOCUMENTS

| | | | |
|---|---|---|---|
| 2010/0237291 A1 | 9/2010 | Simmons et al. | |
| 2010/0270505 A1 | 10/2010 | Gallaspy et al. | |
| 2010/0273899 A1 | 10/2010 | Winter | |
| 2011/0100359 A1* | 5/2011 | North | 127/1 |
| 2011/0104773 A1* | 5/2011 | Chen et al. | 435/161 |
| 2011/0111456 A1* | 5/2011 | Medoff | 435/68.1 |
| 2011/0114876 A1* | 5/2011 | Brady et al. | 252/182.12 |
| 2011/0150722 A1 | 6/2011 | Stites et al. | |
| 2011/0155559 A1* | 6/2011 | Medoff | 204/157.63 |
| 2011/0162376 A1 | 7/2011 | Guo | |
| 2011/0256615 A1* | 10/2011 | Brady et al. | 435/267 |
| 2011/0283705 A1* | 11/2011 | Oliver | 60/698 |
| 2011/0287498 A1* | 11/2011 | Medoff et al. | 435/135 |
| 2012/0023000 A1* | 1/2012 | Rhodes, III | 705/37 |
| 2012/0047794 A1 | 3/2012 | Bartek et al. | |
| 2012/0077247 A1* | 3/2012 | Medoff | 435/209 |
| 2012/0116063 A1* | 5/2012 | Jansen et al. | 530/507 |

OTHER PUBLICATIONS

Higuchi, Takayoshi "Steam Explosion of Wood", Sections 1-4, Biomass Handbook, © 1989 by OPA (Amsterdam), pp. 470-473 plus Cover, Biblio, Table of Contents excerpt. 7 pages total, Editors: Osamu Kitani & Carl W. Hall, ISBN 2-88124-269-3, Gordon and Breach Science Publishers S. A., Cooper Station, New York, New York.

"StakeTech—First Pulping System Receives Full Acceptance", May 14, 1996, 2 pages. Publisher: Business Wire. downloaded from http://www.thefreelibrary.com/StakeTech.

McCallum, Don, "Medium Density Fiber Board" pp. 8-11, Nov. 1, 1996 http://fennerschool-associated.anu.edu.au/fpt/mdf/manufacture.html.

Lam, PS, "Steam Explosion of Biomass to Produce Durable Wood Pellets", The University of British Columbia, May 2011, Retrieved from the Internet on Oct. 21, 2013 from URL https://circle.ubc.ca/bitstream/id/123471/ubc_2011_fall_lam_paksui.pdf. p. 33, Paragraph 1; p. 43, Paragraphs 1-3, Tables 2.4-2.5.

International Search Report for International Application No. PCT/US2013/044143 mailed Nov. 13, 2013, 3 pages. International Searching Authority/US, Alexandria, Virginia USA.

Written Opinion for International Application No. PCT/US2013/044143 mailed Nov. 13, 2013, 15 pages. International Searching Authority/US, Alexandria, Virginia USA.

Restriction Action for U.S. Appl. No. 13/429,847 mailed Apr. 3, 2014, 6 p., U.S. Patent and Trademark Office, Alexandria, VA US.

Non-Final Office Action for U.S. Appl. No. 13/429,847 mailed Aug. 15, 2014, 16 p., U.S. Patent and Trademark Office, Alexandria, VA US.

* cited by examiner

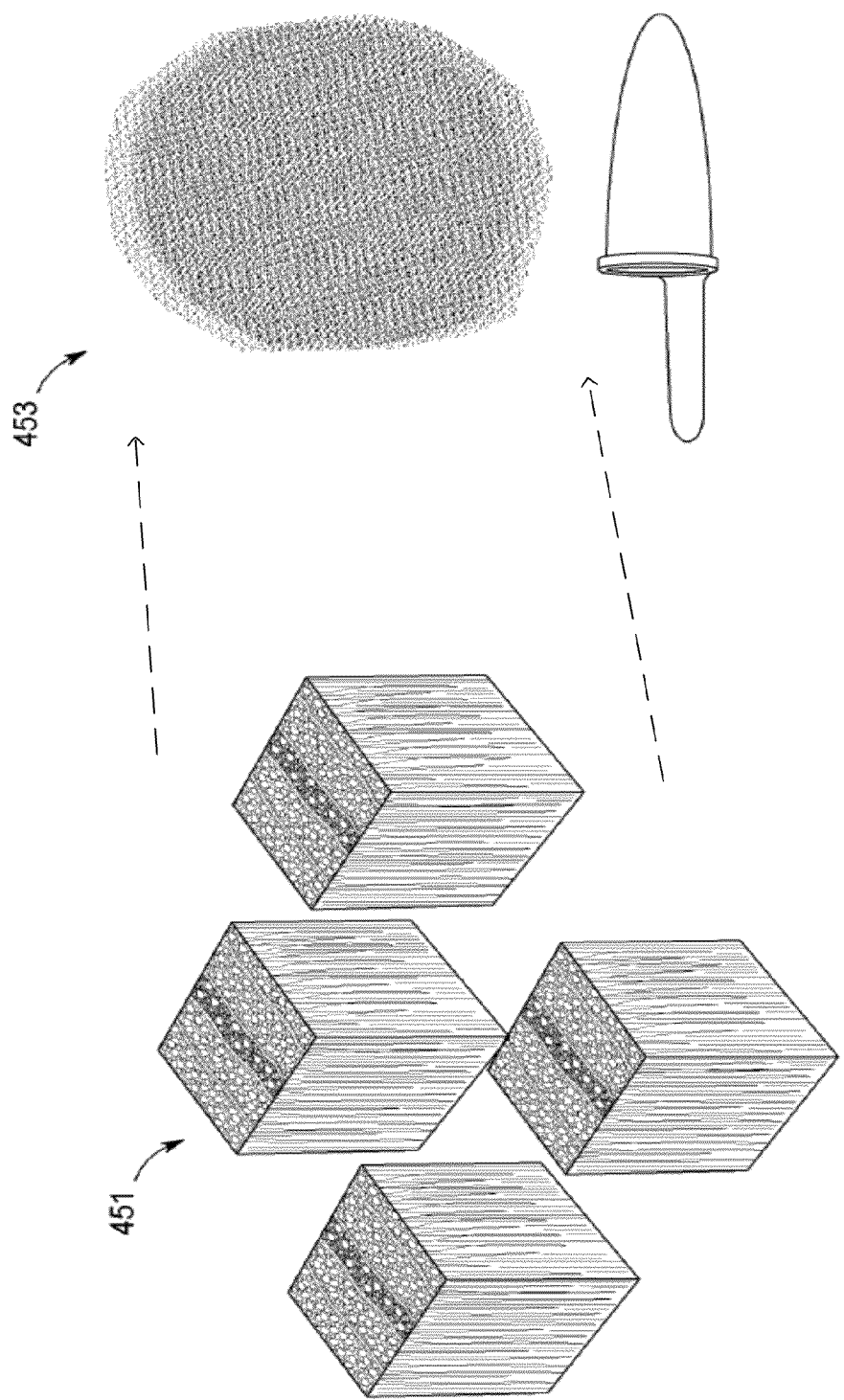

PRETREATMENT OF BIOMASS USING STEAM EXPLOSION METHODS

FIELD

The invention generally relates to treatment of biomass using steam explosion methods as a pre-process before gasification or combustion and in an embodiment specifically to an integrated plant that uses this biomass to produce a liquid fuel from the biomass or to convert the biomass into a densified form to facilitate economic transport to facilities for further processing to liquid fuel, heat/power, animal feed, bedding, or chemicals.

BACKGROUND

The technology was originally conceived to make medium density fiberboard with dry wood chips. Other processes require multiple steps of grinding the wood chips, drying the chips, re-grinding the chips, moisturizing the fibers, densifying the fibers, and then densifying the wood chips (such as in the form of pellets). These processes are complex, capital intensive and require large amounts of energy. Some other typical processes need to dry the chips of biomass and then grind the chips to very small dimensions before sending them to a subsequent heating/processing unit. This drying and grinding takes a lot of energy and capital costs. These processes produce small fibers but ones that are many times the size of the fine particles produced by a Steam Explosion Process (SEP).

SUMMARY

An integrated plant that includes a steam explosion unit and biomass gasifier to generate syngas from biomass. A steam explosion unit applies a combination of heat, pressure, and moisture to the biomass to make the biomass into a moist, fine particle form. The steam explosion unit applies steam with a high pressure to heat and pressurize any gases and fluids present inside the biomass to internally blow apart the bulk structure of the biomass via a rapid depressurization of the biomass with the increased moisture content. Those produced moist, fine particles of biomass are subsequently fed to a feed section of the biomass gasifier, which reacts the biomass particles in a rapid biomass gasification reaction to produce syngas components. Alternatively, the moist, fine particles may be processed into densified forms (such as pellets) to facilitate economic transport to facilities for further processing to liquid fuel, heat/power, animal feed, litter, or chemicals.

BRIEF DESCRIPTION OF THE DRAWINGS

The multiple drawings refer to the example embodiments of the invention.

FIG. 4D illustrates example chips of biomass exploded into fine particles of biomass.

Figure 1:
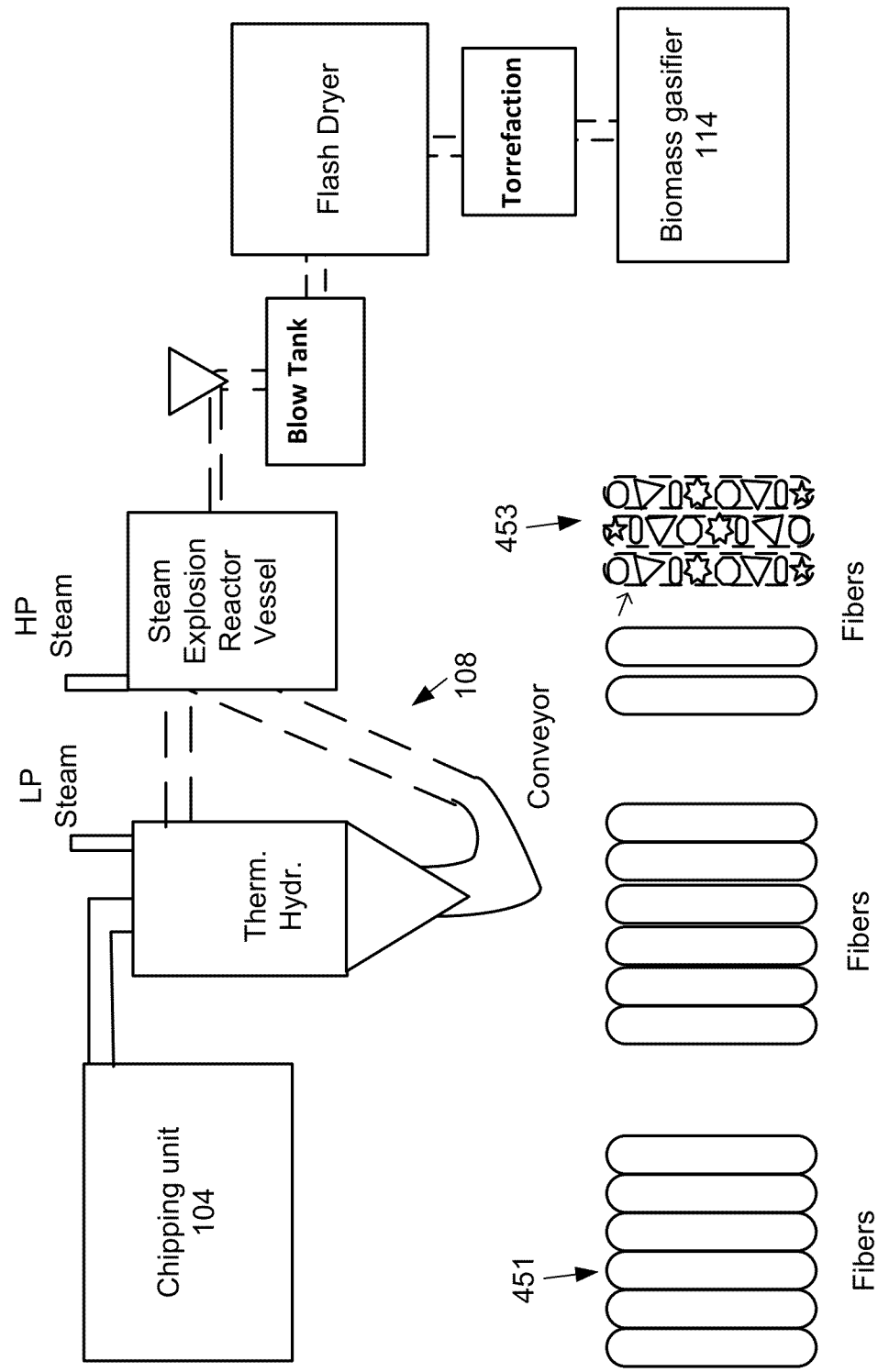
FIG. 1 illustrates a flow schematic of an embodiment of a steam explosion unit having an input cavity to receive biomass as a feedstock, two or more steam supply inputs, and two or more stages to pre-treat the biomass for subsequent supply to a biomass gasifier.

While the invention is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the invention.

DETAILED DISCUSSION

In the following description, numerous specific details are set forth, such as examples of specific chemicals, named components, connections, types of heat sources, etc., in order to provide a thorough understanding of the present invention. It will be apparent, however, to one skilled in the art that the present invention may be practiced without these specific details. In other instances, well known components or methods have not been described in detail but rather in a block diagram in order to avoid unnecessarily obscuring the present invention. Thus, the specific details set forth are merely exemplary. The specific details may be varied from and still be contemplated to be within the spirit and scope of the present invention.

In general, a number of example processes for and apparatuses associated with a pre-treatments of biomass are described. The following drawings and text describe various example implementations for an integrated plant using the pre-treatments of biomass. In an embodiment, the integrated plant contains at least a steam explosion unit and a biomass gasifier to generate syngas from biomass. The steam explosion unit may have an input cavity to receive biomass as a feedstock, one or more steam supply inputs, and two or more stages to pre-treat the biomass for subsequent supply to the biomass gasifier. The stages use a combination of heat, pressure, and moisture that are applied to the biomass to make the biomass into a moist fine particle form. The steam explosion process breaks down a bulk structure of the received biomass, at least in part, by applying steam from a first steam supply input to begin degrading bonds between lignin and hemicellulose from cellulose fibers of the biomass and increase a moisture content of the received biomass. In the last stage, steam at at least ten times atmospheric pressure from a second steam supply input is applied to heat and pressurize any gases and fluids present inside the biomass to internally blow apart the bulk structure of the received biomass via a rapid depressurization of the biomass with the increased moisture content and degraded bonds. The biomass produced into the moist fine particle form from the stages has average dimensions of less than 50 microns thick and less than 500 microns in length. Those produced moist fine particles of biomass are subsequently fed to a feed section of the biomass gasifier. The biomass gasifier has a reactor vessel configured to react the biomass in moist fine particle form with an increased surface area due to being blown apart by the steam explosion unit. The biomass gasifier has a third steam supply input and one or more heaters, and in the presence of the steam the biomass in fine particle form are reacted in the reactor vessel in a rapid biomass gasification reaction in between 0.1 and 5.0 second resident time to produce at least syngas components, including hydrogen (H2) and carbon monoxide (CO).

A possible biomass gasifier implementation has a high temperature steam supply input and one or more regenerative heaters. In the presence of the steam, the particles of the biomass broken down by the steam explosion unit are reacted in the reactor vessel in a rapid biomass gasification reaction at a temperature of greater than 700 degrees C. in less than a one second residence time in the biomass gasifier to create syngas components, including hydrogen (H2) and carbon monoxide (CO), which are fed to a methanol (CH3OH) synthesis reactor. One skilled in the art will understand parts and aspects of many of the designs discussed below within this illustrative document may be used as stand-alone concepts or in combination with each other.

FIG. 1 illustrates a flow schematic of an embodiment of a steam explosion unit having an input cavity to receive biomass as a feedstock, two or more steam supply inputs, and two or more stages to pre-treat the biomass for subsequent supply to a biomass gasifier.

Moisture values in the incoming biomass in chip form can vary from about 15% to 60% for biomass left outside without extra drying. Chips of biomass may be generated by a chipper unit 104 cooperating with some filters with dimensions to create chips of less than about one inch and on average about 0.5 inches in average length and a ¼ inch in thickness on average. (See for example FIG. 4a a chip of biomass 451 from a log of biomass 453) The biomass chipper unit 104 may contain four or more blades used to chop and chip the biomass. The feed speed of the logs of biomass, the speed of the knife blades, the protrusion distance of the knives and the angle of the knives, can all act to control the chip size. The chips are then screened and those that are oversized may be rechipped. There may be a blending of chips from different sources or timber species to enhance certain properties. A magnet or other scanner may be passed over to detect and remove impurities. Chips of biomass are fed on a conveyor or potentially placed in a pressure vessel in the thermally decomposing stage in the steam explosion unit 108 that starts a decomposition, hydrating/moistening, and softening of the chips of biomass using initially low-pressure saturated steam. The low-pressure saturated steam may be at 100 degrees C. The system may also inject some flow aids at this point, such as recycled ash from the biomass gasifier 114, to prevent clogs and plugging by the biomass chips.

The chipper unit 104 may feed to and the steam explosion unit 108 is configured to receive two or more types of biomass feed stocks, where the different types of biomass include 1) soft woods, 2) hard woods, 3) grasses, 4) plant hulls, and 5) any combination that are blended and steam explosion processed into a homogenized torrefied feedstock within the steam explosion unit 108 that is subsequently collected and then fed into the biomass gasifier 114. The steam explosion unit 108, torrefaction unit 112, and biomass gasifier 114 are designed to be feedstock flexible without changing out the physical design of the feed supply equipment or the physical design of the biomass gasifier 114 via at least particle size control of the biomass particles produced from steam explosion stage and torrefaction unit 112.

Figure 4A:
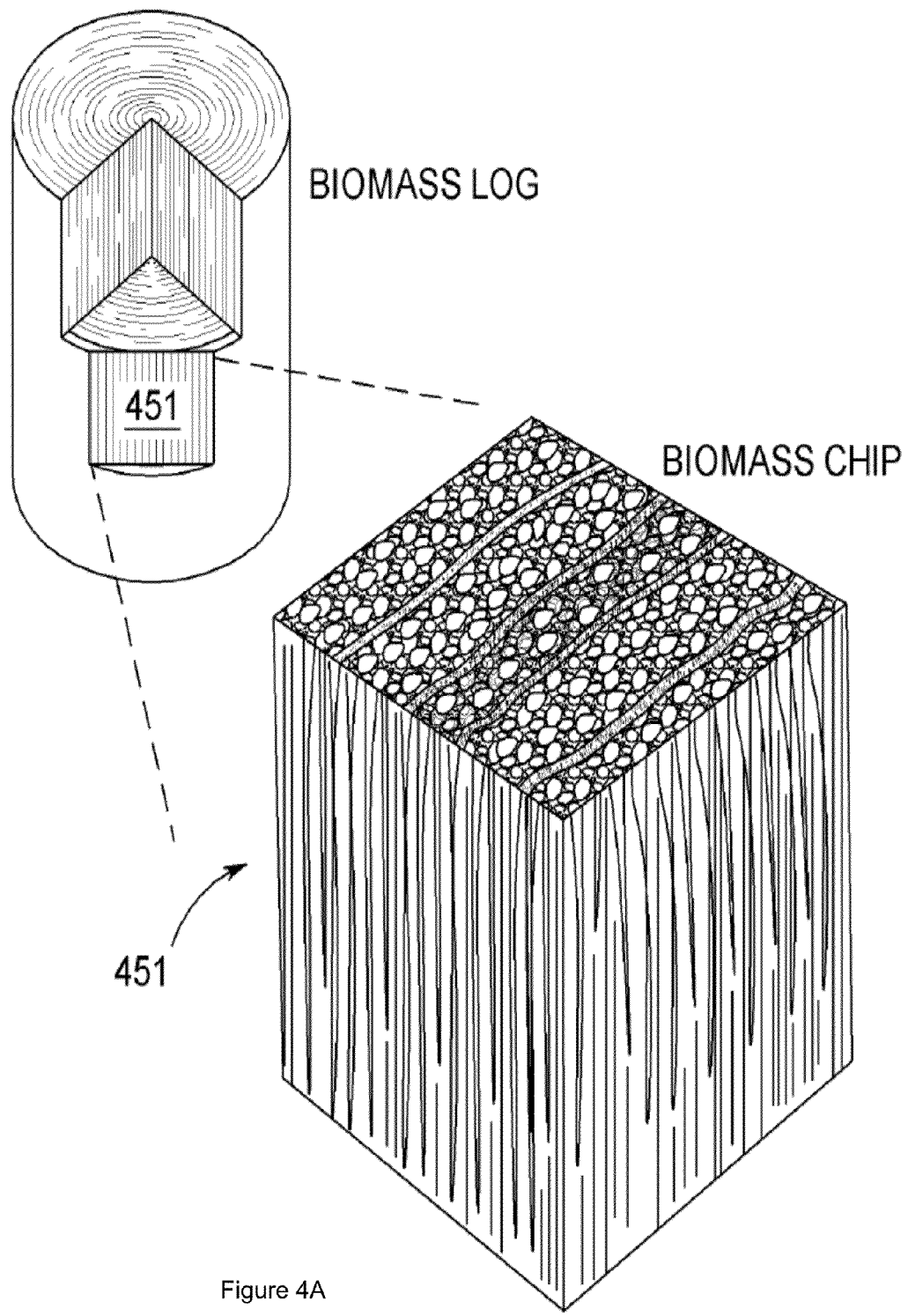
FIGS. 4A-C illustrates different levels of magnification of an example chip of biomass having a fiber bundle of cellulose fibers surrounded and bonded together by lignin.
Figure 4B:
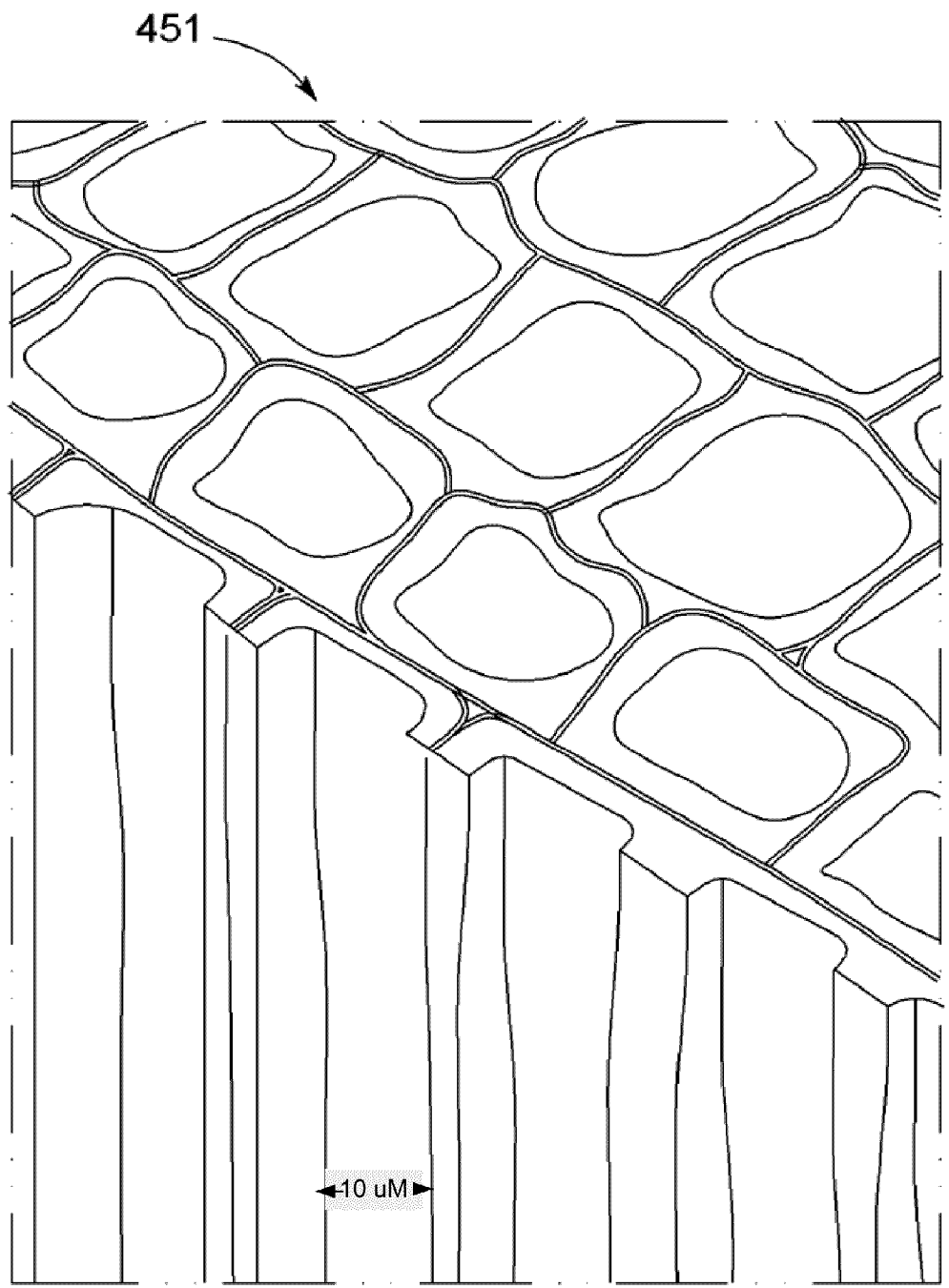

The steam explosion unit 108 has an input cavity to receive biomass as a feedstock, one or more steam supply inputs, and two or more stages to pre-treat the biomass for subsequent supply to a biomass gasifier 114. The stages use a combination of heat, pressure, and moisture that are applied to the biomass to make the biomass into a moist fine particle form. The steam explosion process breaks down a bulk structure of the received biomass, at least in part, by applying steam from a low pressure steam supply input to begin degrading bonds between lignin and hemi-cellulose from cellulose fibers of the biomass and increase a moisture content of the received biomass. (See for example FIG. 4B illustrating a chip of biomass having a fiber bundle of cellulose fibers surrounded and bonded together by lignin.) In the last stage, steam at at least ten times atmospheric pressure from a high pressure steam supply input is applied to heat and pressurize any gases and fluids present inside the biomass to internally blow apart the bulk structure of the received biomass via a rapid depressurization of the biomass with the increased moisture content and degraded bonds.

In an embodiment, the two or more stages of the steam explosion unit 108 include at least a thermally hydrating stage and a steam explosion stage.

The thermally hydrating stage has the input cavity to receive chips of the biomass and the low pressure steam supply input to apply low-pressure saturated steam into a vessel containing the chips of biomass. The thermally hydrating stage is configured to receive the biomass in chip form including leaves, needles, bark, and wood. The thermally hydrating stage applies the low-pressure steam to the biomass at a temperature above a glass transition point of the lignin in order to soften and elevate the moisture content the biomass so the cellulose fibers of the biomass in the steam explosion stage can easily be internally blown apart from the biomass in chip form. In an embodiment, the chips of biomass are heated to greater than 60° C. using the steam. The low pressure steam supply input applies low-pressure saturated steam into a vessel containing the chips of biomass at an elevated temperature of above 60 degrees C. but less than 120 degrees C. at a pressure around atmospheric PSI, to start a decomposition, hydrating, and softening of the received biomass in chip form. The low pressure supply input may consist of several nozzles strategically placed around the vessel. The chips stay in the thermally hydrating stage long enough to saturate with moisture.

Figure 4C:
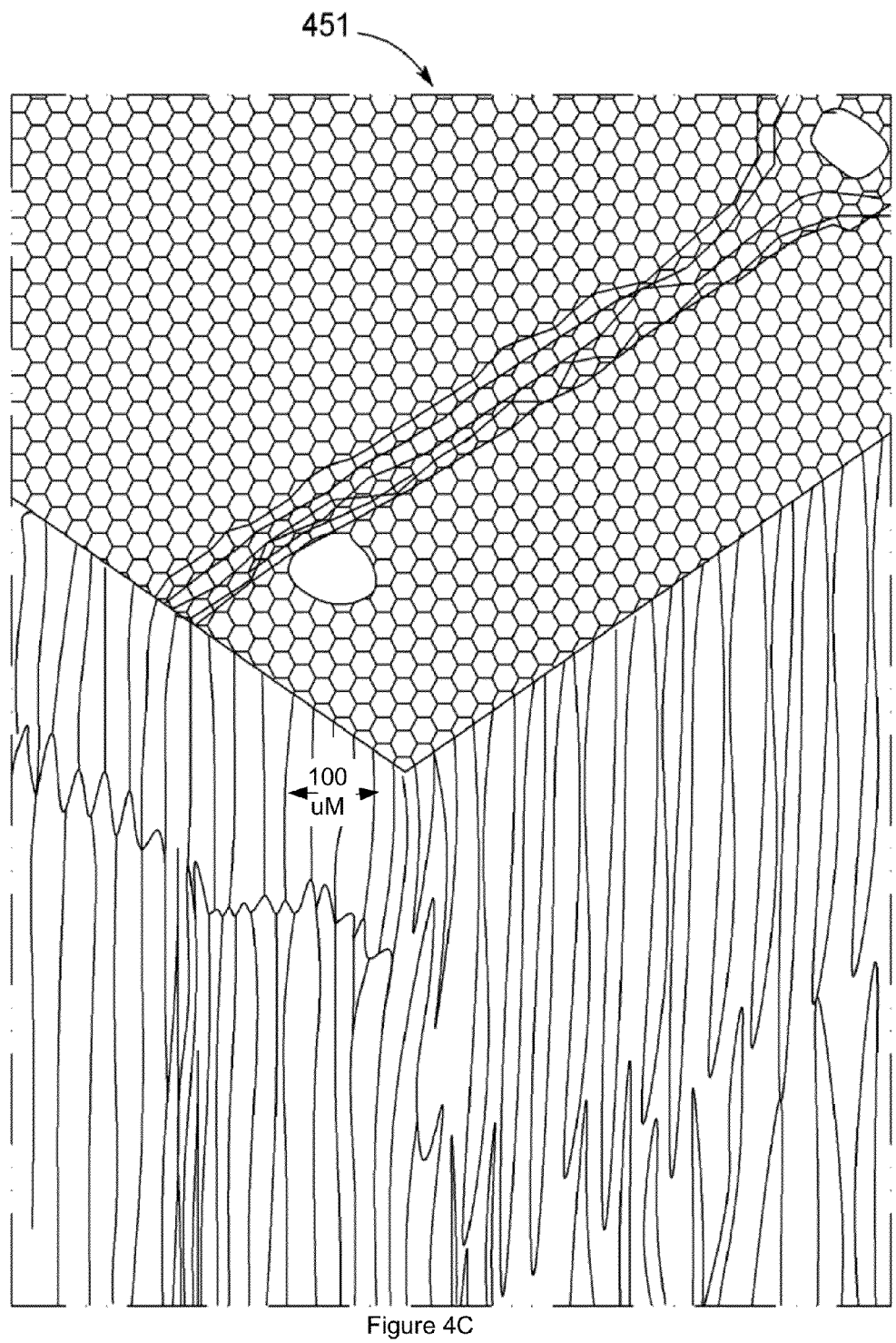

The thermally hydrating stage feeds chips of biomass that have been softened and increased in moisture content to the steam explosion stage, which is at a pressure 10 to 40 times the pressure as is present in the thermally hydrating stage and an elevated temperature, such as a temperature of 160-270° C., 204° C. preferably. The pressure may be at 180-850 Pound per Square Inch (PSI) (256 PSI preferably). The steam explosion stage further raises the moisture content of the plug of biomass to at least 40% by weight and preferably 50 to 55% moisture content by weight. The % moisture by weight may be the weight of water divided by a total weight consisting of the chips of biomass plus a water weight. In the steam explosion stage, the softened and hydrated chips of biomass are exposed to high temperature and high-pressure steam for a sufficient time period, such as 3 minutes to 15 minutes, to create high pressure steam inside the partially hollow cellulose fibers and other porous areas in the bulk structure of the biomass material. (See for example FIG. 4C illustrating a chip of biomass having a fiber bundle of cellulose fibers surrounded and bonded together by lignin but under magnification having numerous porous areas.)

Note, the Steam Explosion Process (SEP) on the biomass chips uses no mechanical refiner to separate fibers; rather, the biomass chip is internally exploded in SEP. Also, no chemical acid additives are added in SEP, such as added acid; and thus, a yield of 88% or greater bagasse may be achieved.

After the thermally hydrating stage, the softened biomass in chip form are any combination of 1) crushed and 2) compressed into a plug form, which is then fed into a continuous screw conveyor system. The continuous screw conveyor system moves the biomass in plug form into the steam explosion stage. The continuous screw conveyor system uses the biomass in plug form to prevent blow back backpressure from the high-pressure steam present in the steam explosion stage from affecting the thermally hydrating stage. Other methods could be used such as 1) check valves and 2) moving biomass in stages where each stage is isolatable by an opening and closing mechanism.

The steam explosion stage can operate at pressures up to 850 psi. The plug screw feeder conveys the chips along the steam explosion stage. High-pressure steam is introduced into the plug screw feeder in a section called the steam mixing conveyor. The high pressure supply input may consist of several nozzles strategically placed around the steam mixing conveyor. Retention time of the biomass chip material through the steam explosion stage is accurately controlled via the plug screw feeder. In the steam explosion stage, the biomass in plug form is exposed to high temperature and high pressure steam at at least 160 degree C. and 160 PSI from the high pressure steam input for at least 5 minutes and preferably around 10 minutes until moisture penetrates porous portions of the bulk structure of the biomass and all of the liquids and gases in the biomass are raised to the high pressure.

As discussed, for the Steam Explosion Process to work properly, the system needs a certain level of humidity/moisture in the biomass chips to provide the source of explosion. So usually, the chip's moisture is generally at least 50 to 55% by weight while in the steam explosion reactor. In the steam explosion stage of the steam explosion unit 108, the pressure and temperature are raised in a chamber containing the chips of biomass with softened lignin to an increased temperature of at least twenty degrees greater than an operating environment of the vessel with chips of biomass in the thermally hydrating stage and to an increased pressure greater than ten times atmospheric in the chamber but for a shorter duration than the set period of time in the thermally hydrating stage.

The continuous screw conveyor system feeds the biomass in plug form through the steam explosion stage to an exit.

In an embodiment, a small opening forms the exit and goes into a tube that is maintained at around atmospheric pressure and any internal fluids or gases at the high pressure expand to internally blow apart the biomass. The pressure at the exit in the steam explosion stage is dropped rapidly by extruding the bulk structure of the biomass at between 160 to 850 PSI into a tube at normal atmospheric pressure to cause an internal "explosion" rapid expansion of steam upon the drop in pressure or due to the "flashing" of liquid water to vapor upon the drop in pressure below its vapor pressure, which internally blows apart the biomass in chip form into minute fine particles of biomass. In another embodiment, the steam explosion reactor portion of the steam explosion stage contains a specialized discharge mechanism configured to "explode" the biomass chip material to a next stage at atmospheric pressure. The discharge mechanism opens to push the biomass from the high-pressure steam explosion reactor out this reactor discharge outlet valve or door into the feed line of the blow tank.

Thus, the pressurized steam or super-heated water out of the steam explosion reactor in this stage is then dropped rapidly to cause an explosion, which disintegrates the chips of biomass into minute fine particles. (See for example FIG. 4D illustrating chips of biomass exploded into fine particles of biomass 453.) The original bundle of fibers making up the biomass is exploded into fragments making discrete particles of fine powder. (See for example FIGS. 4A-C illustrating different levels of magnification of a chip of biomass having a fiber bundle of cellulose fibers surrounded and bonded together by lignin and compare to FIG. 4D.)

The moisture and biomass chips get extruded out the reactor discharge to a container, such as the blow line, at approximately atmospheric pressure. The high-pressure steam or water conversion to vapor inside the partially hollow fibers and other porous areas of the biomass material causes the biomass cell to explode into fine particles of moist powder. The bulk structure of the biomass includes organic polymers of lignin and hemi-cellulose that surrounds a plurality of cellulose fibers. The bulk structure of the biomass is internally blown apart in this SEP step that uses at least moisture, pressure, and heat to liberate and expose the cellulose fibers to be able, as an example, to directly react during the biomass gasification reaction rather than react only after the layers of lignin and hemi-cellulose have first reacted to then expose the cellulose fibers. The high temperatures also lowers the energy/force required to breakdown the biomass' structure as there is a softening of lignin that facilitates fiber separation along the middle lamella.

Thus, internally in the steam explosion stage, a mechanical mechanism opens, such as a valve or door, or merely a small hole exists in the steam explosion reactor. The reactor is filled with softened biomass chips potentially in plug form at high pressure and after a period of time exposes those softened biomass chips to a low pressure that physically blows apart the bulk structure of fiber bundle of the biomass containing the lignin, cellulose fibers, and hemi-cellulose into fragments and separates one from another. When the steam-exposition process operates at lower severities (e.g. 175-185 degrees C. and 160 PSI) in the steam explosion reactor then particles in the size of fragments of small fibers come out of the discharge and at higher severities (e.g. 300 PSI) very, very, fine grains of particles are produced.

The biomass produced into the moist fine particle form from the stages has average dimensions of less than 50 microns thick and less than 500 microns in length. In an embodiment, the produced fine particles of biomass with reduced moisture content includes cellulose fibers that are fragmented, torn, shredded and any combination of these and may generally have an average dimension of less than 30 microns thick and less than 250 microns in length. Those produced moist fine particles of biomass are subsequently fed to a feed section of the biomass gasifier 114.

Internally blowing apart the bulk structure of biomass in a fiber bundle into pieces and fragments of cellulose fiber, lignin and hemi-cellulose results in all three 1) an increase of a surface area of the biomass in fine particle form compared to the received biomass in chip form, 2) an elimination of a need to react outer layers of lignin and hemi-cellulose prior to starting a reaction of the cellulose fibers, and 3) a change in viscosity of the biomass in fine particle form to flow like grains of sand rather than like fibers.

The morphological changes to the biomass coming out of SEP reactor can include:
  a. No intact fiber structure exists rather all parts are exploded causing more surface area, which leads to higher reaction rates in the biomass gasifier;

b. Fibers appear to buckle, they delaminate, and cell wall is exposed and cracked;
c. Some lignin remains clinging to the cell wall of the cellulose fibers;
d. Hemi-cellulose is partially hydrolyzed and along with lignin are partially solubilized;
e. The bond between lignin and carbohydrates/polysaccharides (i.e. hemi-cellulose and cellulose) is mostly cleaved; and
f. many other changes discussed herein.

The created moist fine particles may be, for example, 20-50 microns thick in diameter and less than 100 microns in length on average. Note, 1 inch=25,400 microns. Thus, the biomass comes from the chipper unit 104 as chips up to 1 inch in length and 0.25 inches in thickness on average and go out as moist fine particles of 20-50 microns thick in diameter and less than 100 microns in length on average, which is a reduction of over 2000 times in size. The violent explosive decompression of the saturated biomass chips occurs at a rate swifter than that at which the saturated high-pressure moisture in the porous areas of the biomass in chip form can escape from the structure of biomass.

Figure 4E:
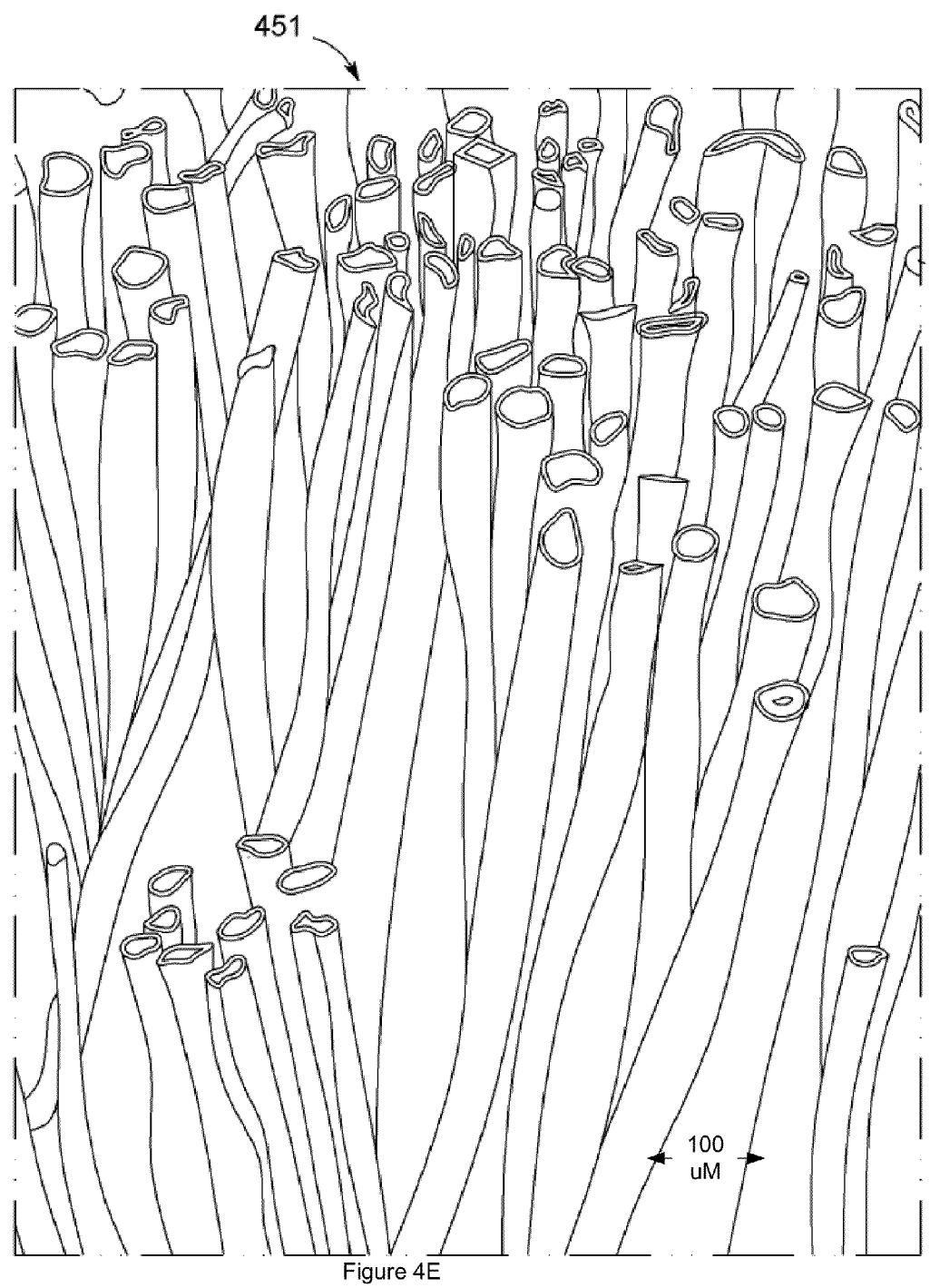
FIG. 4E illustrates a chip of biomass having a bundle of fibers that are frayed or partially separated into individual fibers.

Note, no external mechanical separation of cells or fibers bundle is needed rather the process uses steam to explode cells from inside outward. (See FIG. 4E illustrating a chip of biomass a chip of biomass 451 having a bundle of fibers that are frayed or partially separated into individual fibers.) Use of SEP on the biomass chips produces small fine particles of cellulose and hemi-cellulose with some lignin coating. (See FIG. 4D illustrating example chips of biomass, including a first chip of biomass 451, exploded into fine particles of biomass 453.) This composite of lignin, hemi-cellulose, and cellulose in fine form has a high surface area that can be moved/conveyed in the system in a high density.

The produced fine particles of biomass are fed downstream to the biomass gasifier 114 for the rapid biomass gasification reaction in a reactor of the biomass gasifier 114 because they create a higher surface to volume ratio for the same amount of biomass compared to the received biomass in chip form, which allows a higher heat transfer to the biomass material and a more rapid thermal decomposition and gasification of all the molecules in the biomass.

In an embodiment, cyclic operations are possible rather than a continuous conveyor system. The cyclic operation allows soft moist chips to be loaded into the SEP reactor and then the steam input introduces high temperature and high-pressure steam for 10 minutes to raise the pressure of the gases and liquids in the biomass. After that period, the valve or door opens to extrude biomass particles into feed line into blow tank.

A collection chamber at an outlet stage of the steam explosion stage is used to collect the biomass reduced into smaller particle sizes and in pulp form. One or more cyclone filters can be in line with the feed line to separate water vapor from biomass particles, where biomass particles are then fed into a blow tank.

As discussed, at an exit of the steam explosion stage, once the biomass in plug form explodes into the moist fine particles form. The steam explosion stage filled with high-pressure steam and/or superheated water contains a discharge outlet configured to "explode" the biomass material to a next stage at atmospheric pressure to produce biomass in fine particle form. The biomass in fine particle form flows through a feed line of a blow tank at high velocity.

The biomass in moist fine particles form enters the feed line of the blow tank. The feed line is initially small, such as only 1.5 in. in diameter, with the particles of the biomass passing through at high velocity. Flow enhancements, such as wax, may be added in initial portion of the blow line while the fibers are still wet to improve material consistency and avoid hydro bonding. The feed line now expands to 60 in. in diameter and the biomass in moist fine particles form has its heat maintained by heating coils traced around and warming the blow line. Maintaining the temperature of the biomass tends to help crystallize the rosins and resin acids of the biomass preventing the fiber particles from conglomerating back together. Thus, the temperature helps to prevent the lignin from clumping and rosins from hardening.

The flow aids, including any of 1) ash recycled from the biomass gasifier 114 and 2) olephins, such as wax, are injected at any of 1) the discharge outlet of the steam explosion stage and 2) in the feed line to prevent clogs by the biomass. In addition, the feed line may have heating coils traced around the feed line to maintain an elevated temperature of the biomass in fine particle form to help prevent crystallization of rosins and resin acids in the biomass in fine particle form.

The produced particles of biomass loses a large percentage of the moisture content due to steam flashing in the blow line and being vented off as a water vapor. The produced particles of biomass and moisture are then separated by a cyclone filter and then fed into a blow tank. Thus, a water separation unit is inline with the blow line. A collection chamber at an outlet stage of the steam explosion stage is used to collect the biomass reduced into smaller particle sizes and in pulp form and is fed to the water separation unit. Water is removed from the biomass in fine particle form in a cyclone unit or a flash dryer.

A moisture content of the fine particles of biomass is further dried out at an exit of the blow tank by a flash dryer that reduces the moisture content of fine particles of biomass to 5-20% by weight preferably and up to 35% in general. A goal of the fiber preparation is to create particles of biomass with maximum surface area and as dry as feasible to 5-20% moisture by weight of the outputted biomass fine particle. The flash dryer merely blows hot air to dry the biomass particles coming out from the blow tank. The flash dryer can be generally located at the outlet of the blow tank or replace the cyclone at its entrance to make the outputted biomass particles contain a greater than 5% but less than 35% moisture content by weight.

The resulting particles of biomass differs from Thermal Mechanical Pulping (TMP) in that particles act more like crystal structures and flows easier than fibers which tend to entangle and clump.

The reduced moisture content of 5% to about 35% by weight of the biomass in fine particle form is fed by a conveying system, as an example, to a torrefaction unit 112 to undergo torrefaction or pyrolysis at a temperature from 100 to 700 degrees C. for a preset amount of time.

A conveyor system supplies the biomass in particle form to a torrefaction unit 112 to process the biomass at a temperature of less than 700 degrees C. for a preset amount of time to create off gases to be used in a creation of a portion of the syngas components that are collected by a tank and may be eventually fed to the methanol synthesis reactor.

The fine particles of biomass out of the blow tank and flash dryer has a low moisture content already due to the steam flashing, further air drying, and are a composite of fragments of cellulose fibers with a lignin coating, pieces of lignin, cellulose, and hemi-cellulose, etc. The biomass gasifier 114 has a reactor vessel configured to react the biomass in moist fine particle form with an increased surface area due to being blown apart by the steam explosion unit 108. The biomass gasifier 114 has a high pressure steam supply input and one or more heaters, and in the presence of the steam the biomass in fine particle form are reacted in the reactor vessel in a rapid biomass gasification reaction between 0.1 and 5.0 second resident time to produce at least syngas components, including hydrogen ($H_2$) and carbon monoxide (CO). When the fine particles produced are supplied in high density to the biomass gasifier 114, then the small particles react rapidly and decompose the larger hydrocarbon molecules of biomass into the syngas components more readily and completely. Thus, nearly all of the biomass material lignin, cellulose fiber, and hemi-cellulose completely gasify rather than some of the inner portions of the chip not decomposing to the same extent to that the crusted shell of a char chip decomposes. These fine particles compared to chips create less residual tar, less carbon coating and less precipitates. Thus, breaking up the integrated structure of the biomass in a fiber bundle tends to decrease an amount of tar produced later in the biomass gasification. These fine particles also allow a greater packing density of material to be fed into the biomass gasifier 114. As a side note, having water as a liquid or vapor present at at least 10 percent by weight may assist in generating methanol $CH_3OH$ as a reaction product in addition to the CO and $H_2$ produced in the biomass gasifier 114.

The torrefaction unit and biomass gasifier 114 may be combined as an integral unit.

In the alternative, the moist blown apart particles of biomass may be fed in slurry form from the output of the steam explosion reactor directly, or after drying, to a pelletizer. The pelletizer may densify the biomass from form into pellets of biomass, which those pellets are then fed into the biomass gasifier. This direct feed and conversion of biomass from form to pellet form saves multiple steps and lots of energy consumption involved in those eliminated steps. Alternatively, the pellets may be transported to facilities for further processing to liquid fuel, heat/power, animal feed, litter, or chemicals.

In an embodiment, the biomass gasifier 114 is designed to radiantly transfer heat to particles of biomass flowing through the reactor design with a rapid gasification residence time, of the biomass particles of 0.1 to 10 seconds and preferably less one second. The biomass particles and reactant gas flowing through the radiant heat reactor primarily are driven from radiant heat from the surfaces of the radiant heat reactor and potentially heat transfer aid particles entrained in the flow. The reactor may heat the particles in a temperature in excess of generally 900 degrees C. and preferably at least 1200° C. to produce the syngas components including carbon monoxide and hydrogen, as well as keep produced methane at a level of ≤1% of the compositional makeup of exit products, minimal tars remaining in the exit products, and resulting ash.

An example Particle Size Analysis to determine the particle size can be a Digital Image Processing Particle Size and Shape Analysis System such as a Horiba Camsizer XT particle size analyzer. Such a system uses one or more cameras to provide rapid and precise particle size and particle shape distributions for dry powders and bulk material in the size range, for example, from 30 µm to 30 mm. The measurements from the digital image processing system allows a correlation to existing data from techniques as diverse as sieving and sedimentation, which in some instances may also be used to measure particle size. In an embodiment, the particle size of the steam exploded wood chips are measured using a Horiba Camsizer XT particle size analyzer. The sample to be measured is mixed in a resealable bag by kneading and agitating the material in the bag by external manipulation. After mixing, a sample amount, such as approximately 3 cm^3, is loaded into the sample hopper of the instrument. The target is to run and analyze enough sample size, such as at least 2 million particles from each sample, so the sample volume is only important insofar as it corresponds to an adequate number of particles. Example settings on the instrument can be as follows 0.2% covered area, image rate 1:1, with X-Jet, gap width=4.0 mm, dispersion pressure=380.0 kPa, xFe_max [and xc_min, accordingly]. Feed rate is controlled to yield a target covered area so that the computer can process the images quickly enough. The camera imaging rate is fixed, and both "basic" and zoom images are obtained for every run. A single value for average particle size, such as the diameter is less than 50 microns, may be the objective measurement standard. In an embodiment, a three point value for both Fe-max and xc-min is more complete. So that's like a 6 point value. The particle size distribution (PSD) may be defined as Fe-Max D10, D50, D90 and Xc-min D10, D50, D90. The measurement then can use multiple values such as input 6 values to determine the measurement. Other similar mechanisms may be used.

Calculations can be made using Fe max and xc min on a volume basis. Two models can be used to analyze the particle images: xc-min, which yields results comparable to those obtained by physically screening/sieving samples, and Fe-max, which is similar to measuring the longest dimension of a given particle with a caliper. Raw data, frequency plots, binned results, and particle images are obtained for all samples. D10, D50, and D90 may be calculated on a volume basis, as is the average aspect ratio. D90 describes the diameter where ninety percent of the distribution has a smaller particle size and ten percent has a larger particle size. The D10 diameter has ten percent smaller and ninety percent larger. A three point specification featuring the D10, D50, and D90 is considered complete and appropriate for most particulate materials. In an embodiment, the particle size distribution PSD may be defined as D50 (µm) Model Fe-max.

TABLE 1

Particle size distributions for steam exploded wood
Particle size indices for SEP-processed samples generated from
xc-min and Fe-max models.

| Example | Model | D10 (µm) | D50 (µm) | D90 (µm) | Avg. Aspect |
| --- | --- | --- | --- | --- | --- |
| SEP White Pine #1 | xc-min | 20.4 | 59.8 | 176 | 0.47 |
| SEP White Pine #2 | xc-min | 23.9 | 71.7 | 213 | 0.48 |
| SEP White Pine #2-a | xc-min | 21.7 | 65.3 | 197 | 0.49 |
| SEP White Pine #3 | xc-min | 23 | 59.5 | 182 | 0.47 |
| SEP Mixed Hardwood #4 | xc-min | 39.3 | 175.0 | 404.1 | — |
| SEP Black Spruce #5 | xc-min | 25.6 | 94.4 | 320 | 0.45 |
| SEP White Pine #1 | Fe-max | 34.5 | 158 | 541 | 0.47 |
| SEP White Pine #2 | Fe-max | 41.4 | 186 | 660 | 0.45 |
| SEP White Pine #2-a | Fe-max | 39.2 | 176 | 584 | 0.46 |
| SEP White Pine #3 | Fe-max | 42.9 | 186 | 629 | 0.45 |
| SEP Mixed Hardwood #4 | Fe-max | 37 | 168 | 397 | — |
| SEP Black Spruce #5 | Fe-max | 44.7 | 238 | 878 | 0.44 |

The examples in Table 1 were produced with a Steam Pressure of 16 bar and a reaction time of 10 minutes.

Figure 2:
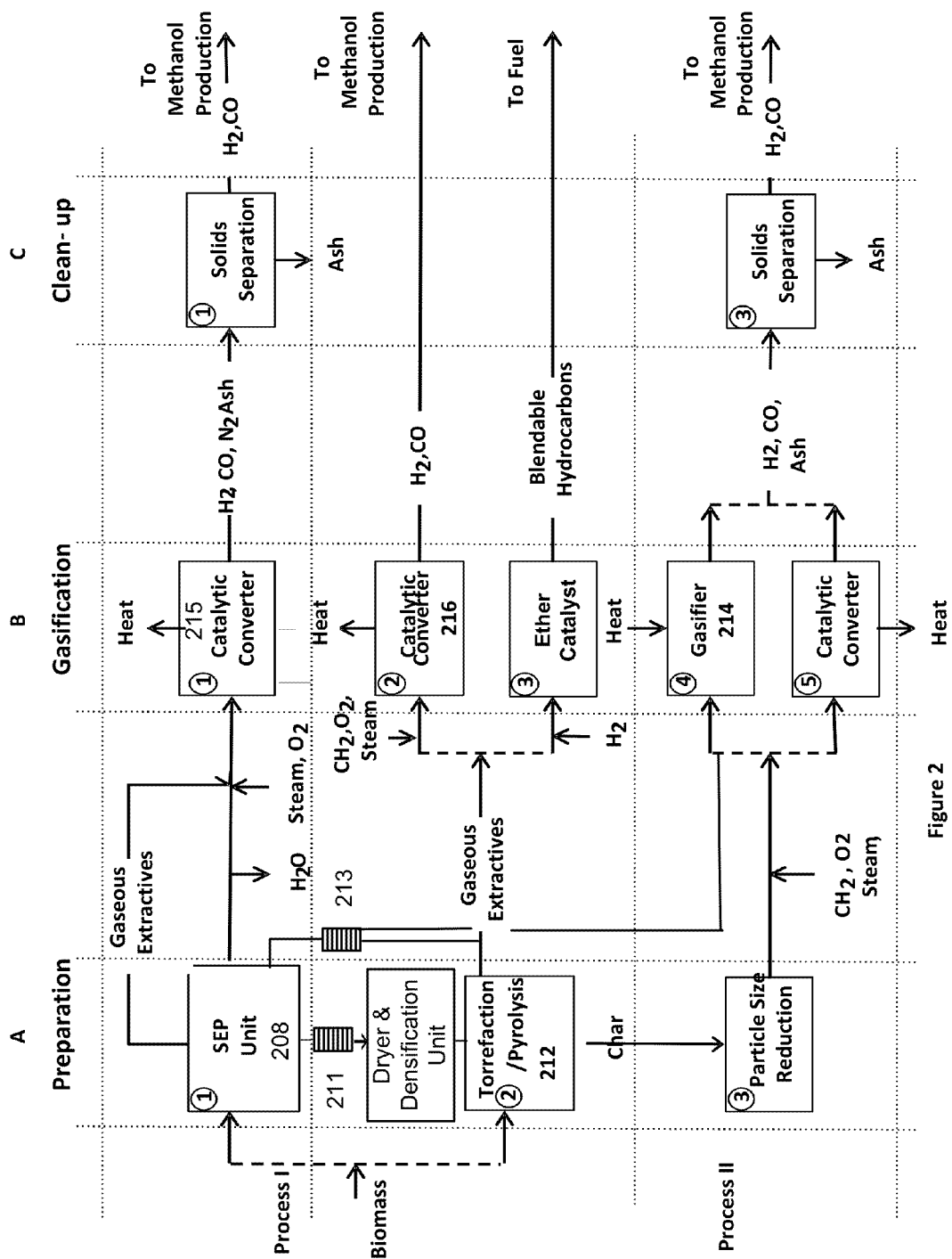
FIG. 2 illustrates a flow schematic of an embodiment of a steam explosion unit having a steam explosion stage that supplies particles of biomass to either a dryer, the torrefaction unit, a densification unit, the biomass gasifier, or to a catalytic converter.

FIG. 2 illustrates a flow schematic of an embodiment of a steam explosion unit 108 having a steam explosion stage and thermally hydrating stage that supplies particles of biomass to either a torrefaction unit, or to the biomass gasifier 114, or to a catalytic converter.

A conveying system coupled to a collection chamber at the outlet stage of the steam explosion unit 208 supplies particles of biomass in particle form to either a torrefaction unit 212, or to the biomass gasifier 214, or to a catalytic converter 215. A majority of the initial lignin and cellulose making up the biomass in the receiver section of the steam tube stage in the steam explosion unit 208 remains in the produced particles of biomass but now substantially separated from the cellulose fibers in the collection chamber at the outlet stage of the steam explosion stage 208.

The collection chamber in the steam explosion unit 208 is configured to collect non-condensable hydrocarbons from any off gases produced from the biomass during the steam explosion process.

Figure 3A:
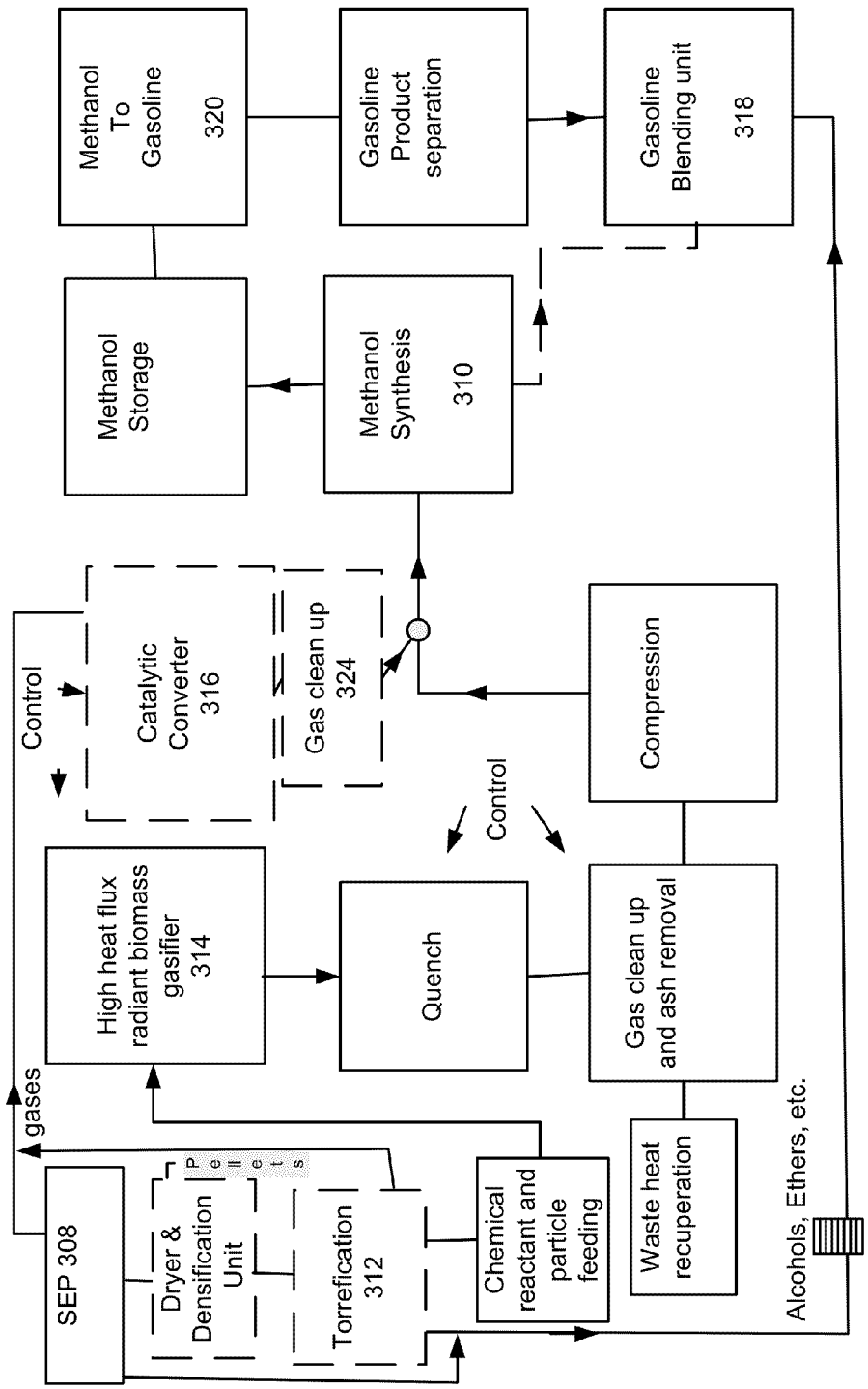
FIGS. 3A and 3B illustrate embodiments of flow diagrams of an integrated plant to generate syngas from biomass and generate a liquid fuel product from the syngas, or biomass in a densified form.

After the steam explosion stage 208, water is removed from the biomass in a water separation unit 211, for example a cyclone unit, and the reduced moisture content biomass made of loose fibers and separated lignin and cellulose may be fed to a torrefaction unit 212 to under go multiple stages of torrefaction. Condensable hydrocarbons including alcohols, ethers, and other C5 hydrocarbons may be separated by a filter unit 213 from the water removed from the biomass and then the condensable hydrocarbons are sent to a gasoline blending unit FIG. 3A illustrates an embodiment of a flow diagram of an integrated plant to generate syngas from biomass and generate a liquid fuel product from the syngas.

In an embodiment, one or more gas collection tanks in the steam explosion unit 308 may collect non-condensable hydrocarbons from any off gases produced from the biomass during the SEP process and send those non-condensable hydrocarbons with any collected in the torrefaction unit 312 to a catalytic converter 316.

In another embodiment, the reduced moisture content pulp may go directly from the steam explosion unit 308 to the biomass gasifier 314, a torrefaction unit 312, or to a catalytic converter 316. Generally, the particles of biomass go to the torrefaction unit 312 and then onto the biomass gasifier 314. However, the torrefaction unit 312 and biomass gasifier may be combined into a single unit.

The general compositions of biomass types that can be blended, for example, include:

| Component | Wood | Non-wood |
|---|---|---|
| Cellulose | 40-45% | 30-45% |
| Hemi cellulose | 23-35% | 20-35% |
| Lignin | 20-30% | 10-25% |

The biomass gasifier 314 has a reactor configured to react particles of the biomass broken down by the two or more stages of the steam explosion unit 308 and those biomass particles are subsequently fed to a feed section of the biomass gasifier 314. The biomass gasifier 314 has a high temperature steam supply input and one or more regenerative heaters and in the presence of the steam the particles of the biomass broken down by the steam explosion unit 308 are reacted in the reactor vessel in a rapid biomass gasification reaction at a temperature of greater than 700 degrees C. in less than a five second residence time in the biomass gasifier 314 to create syngas components, including hydrogen (H2) and carbon monoxide (CO), which are fed to a methanol (CH3OH) synthesis reactor 310. In the gasifier 314, the heat transferred to the biomass particles made up of loose or fragments of cellulose fibers, lignin, and hemicellulose no longer needs to penetrate the layers of lignin and hemicellulose to reach the fibers. In some embodiments, the rapid biomass gasification reaction occurs at a temperature of greater than 700 degrees C. to ensure the removal tars from forming during the gasification reaction. Thus, a starting temperature of 700 degrees but less than 950 degrees is potentially a significant range of operation for the biomass gasifier. All of the biomass gasifies more thoroughly and readily.

The biomass gasifier 314 may have a radiant heat transfer to particles flowing through the reactor design with a rapid gasification residence time, of the biomass particles of 0.1 to 10 seconds and preferably less one second, of biomass particles and reactant gas flowing through the radiant heat reactor, and primarily radiant heat from the surfaces of the radiant heat reactor and particles entrained in the flow heat the particles and resulting gases to a temperature in excess of generally 700 degrees C. and preferably at least 1200° C. to produce the syngas components including carbon monoxide and hydrogen, as well as keep produced methane at a level of ≤1% of the compositional makeup of exit products, minimal tars remaining in the exit products, and resulting ash. In some embodiments, the temperature range for biomass gasification is greater than 800 degrees C. to 1400 degrees C.

Referring to FIG. 2, the plant uses any combination of the three ways to generate syngas for methanol production. Syngas may be a mixture of carbon monoxide and hydrogen that can be converted into a large number of organic compounds that are useful as chemical feed stocks, fuels and solvents. 1) The steam explosion unit 208 and/or torrefaction of biomass causes off gases to be fed to a catalytic converter 216 that can generate hydrogen and carbon monoxide for methanol production. 2) The biomass gasifier 214 gasifies biomass at high enough temperatures to eliminate a need for a catalyst to generate hydrogen and carbon monoxide for methanol production. 3) Alternatively, a lower temperature catalytic conversion of particles of biomass may be used to generate hydrogen and carbon monoxide for methanol production. Similarly, the steam explosion process and torrefaction process may be used to generate condensable hydrocarbons for use in gasoline blending to increase the octane of the final gasoline product.

Note, olefins may be any unsaturated hydrocarbon, such as ethylene, propylene, and butylenes, containing one or more pairs of carbon atoms linked by a double bond. Olefins may have the general formula $CnH2n$, C being a carbon atom, H a hydrogen atom, and n an integer.

The torrefaction unit 212 has two or more areas to segregate out and then route the non-condensable gases including the C1 to C4 olefins, as well as other gases including CO, CH4, CO2 and H2, through a supply line to the catalytic converter 216 that catalytically transform portions of the non-condensable gases to the syngas components of CO, H2, CO2 in small amounts, and potentially CH4 that are sent in parallel with the portion of syngas components from the biomass gasifier 214 to a combined input to the methanol synthesis reactor. The catalytic converter 216 has a control system to regulate a supply of an oxygenated gas and steam along with the non-condensable gases to the catalytic converter 216, which produces at least H2, and CO as exit gases. The catalytic converter 216 uses the control system and the composition of a catalyst material inside the catalytic converter 216 to, rather than convert the supplied non-condensable gases completely into CO2 and H2O in the exit gas, the non-condensable gases, steam, and oxygenated gas are passed through the catalytic converter 216 in a proper ratio to achieve an equilibrium reaction that favors a production of carbon monoxide (CO) and hydrogen (H2) in the exit gas; and thus, reclaim the valuable Renewable Identification Number (RIN) credits associated with the non-condensable gases. RIN credits are a numeric code that is generated by the producer or importer of renewable fuel representing gallons of renewable fuel produced using a renewable energy crop, such as biomass. The primary negative of torrefaction in prior suggestions is the loss of carbon and the associated RIN credits in the volatile materials removed by torrefaction.

Biomass gasification is used to decompose the complex hydrocarbons of biomass into simpler gaseous molecules, primarily hydrogen, carbon monoxide, and carbon dioxide. Some char, mineral ash, and tars are also formed, along with methane, ethane, water, and other constituents. The mixture of raw product gases vary according to the types of biomass feedstock used and gasification processes used. The product gas must be cleaned of solids, tars, and other contaminants sufficient for the intended use.

Referring to FIG. 3A, the biomass gasifier has a gas clean up section to clean ash, sulfur, water, and other contaminants from the syngas gas stream exiting the biomass gasifier 314. The syngas is then compressed to the proper pressure needed for methanol synthesis. The syngas from the catalytic converter 316 may connect upstream or downstream of the compression stage.

The synthesis gas of H2 and CO from the gasifier and the catalytic converter 316 exit gases are sent to the common input to the one or more methanol synthesis reactors. The exact ratio of Hydrogen to Carbon monoxide can be optimized by a control system receiving analysis from monitoring equipment on the compositions of syngas exiting the biomass gasifier 314 and catalytic converters 316 and causing the optimize the ratio for methanol synthesis. The methanol produced by the one or more methanol synthesis reactors is then processed in a methanol to gasoline process.

The liquid fuel produced in the integrated plant may be gasoline or another such as diesel, jet fuel, or some alcohols.

The torrefaction unit 312 may have its own several discrete heating stages. Each heating stage is set at a different operating temperature, rate of heat transfer, and heating duration, within the unit in order to be matched to optimize a composition of the non-condensable gases and condensable volatile material produced from the biomass in that stage of the torrefaction unit 312. Each stage has one or more temperature sensors to supply feedback to a control system for the torrefaction unit 312 to regulate the different operating temperatures and rates of heat transfer within the unit.

Many optional stages may be part of the integrated plant including but not limited to the catalytic converter, the densification unit, the torrefaction unit, etc. Pellets of biomass may be taken directly out of the densification unit and used for many purposes.

Figure 3B:
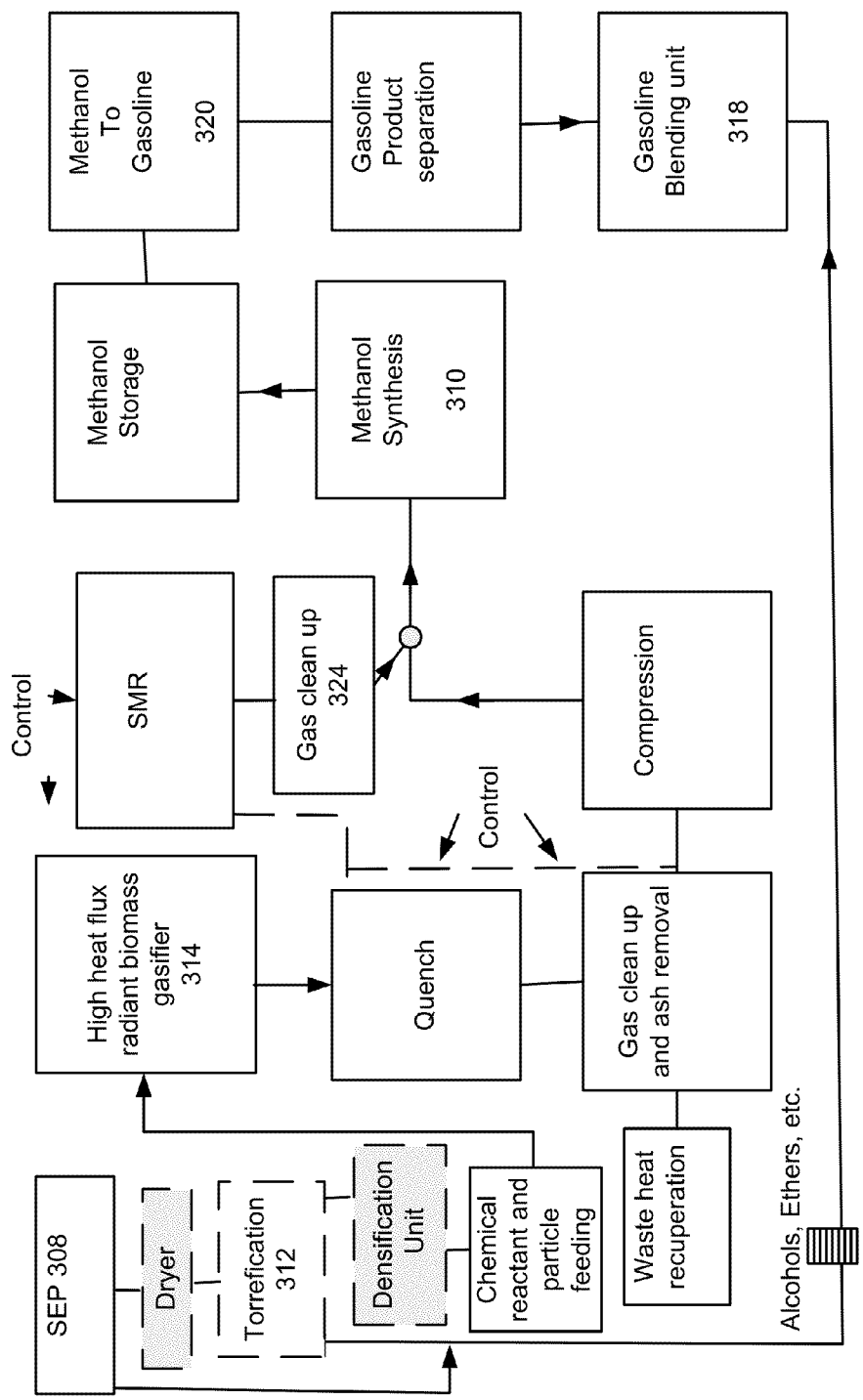

FIG. 3B illustrates an embodiment of a flow diagram of an integrated plant to generate syngas from biomass, and/or to generate biomass in densified form. The integrated plant may have a steam reformation unit in parallel with the biomass gasifier. The SEP unit may supply biomass in fine particle form to a densification unit. The densification unit creates biomass in densified form including but not limited to biomass in pellets.

Thus, a feed system may feed the moist fine particles of biomass in slurry form from an output of the steam explosion unit directly to a densification unit. The densification unit is configured to densify the moist biomass in fine particle form into denser forms, including but not limited to pellets of biomass. Note, an optional dryer unit may be between the SEP unit and the densification unit or located after the densification unit. The biomass in densified pellet form is then fed into one or more of 1) a biomass gasifier, 2) a combustion unit for process heat, 3) a combustion unit to generate electric power, 4) a process unit to produce chemicals, 5) a packaging unit to box and sell as animal feed, litter, or fuel.

As FIGS. 3a and 3b show multiple stages are optional. For instance, the integrated plant may have a SEP unit feeding an optional densification Unit, then to an optional Torrefaction unit, and then to the rest of the plant. In another instance, the integrated plant may have a SEP unit feeding a dryer unit followed by a densification unit that feeds one or more of 1) a biomass gasifier, 2) a combustion unit for process heat, 3) a combustion unit to generate electric power, 4) a process unit to produce chemicals, 5) a packaging unit to box and sell as animal feed, litter or fuel. In another example instance, the SEP unit feeds a dryer unit followed by a torrefaction unit, followed by a densification unit that feeds the rest of the plant.

FIGS. 4A-C illustrates different levels of magnification of an example chip of biomass 451 having a fiber bundle of cellulose fibers surrounded and bonded together by lignin.

FIG. 4D illustrates example chips of biomass, including a first chip of biomass 451, exploded into fine particles of biomass 453.

FIG. 4E illustrates a chip of biomass 451 having a bundle of fibers that are frayed or partially separated into individual fibers.

Figure 5:
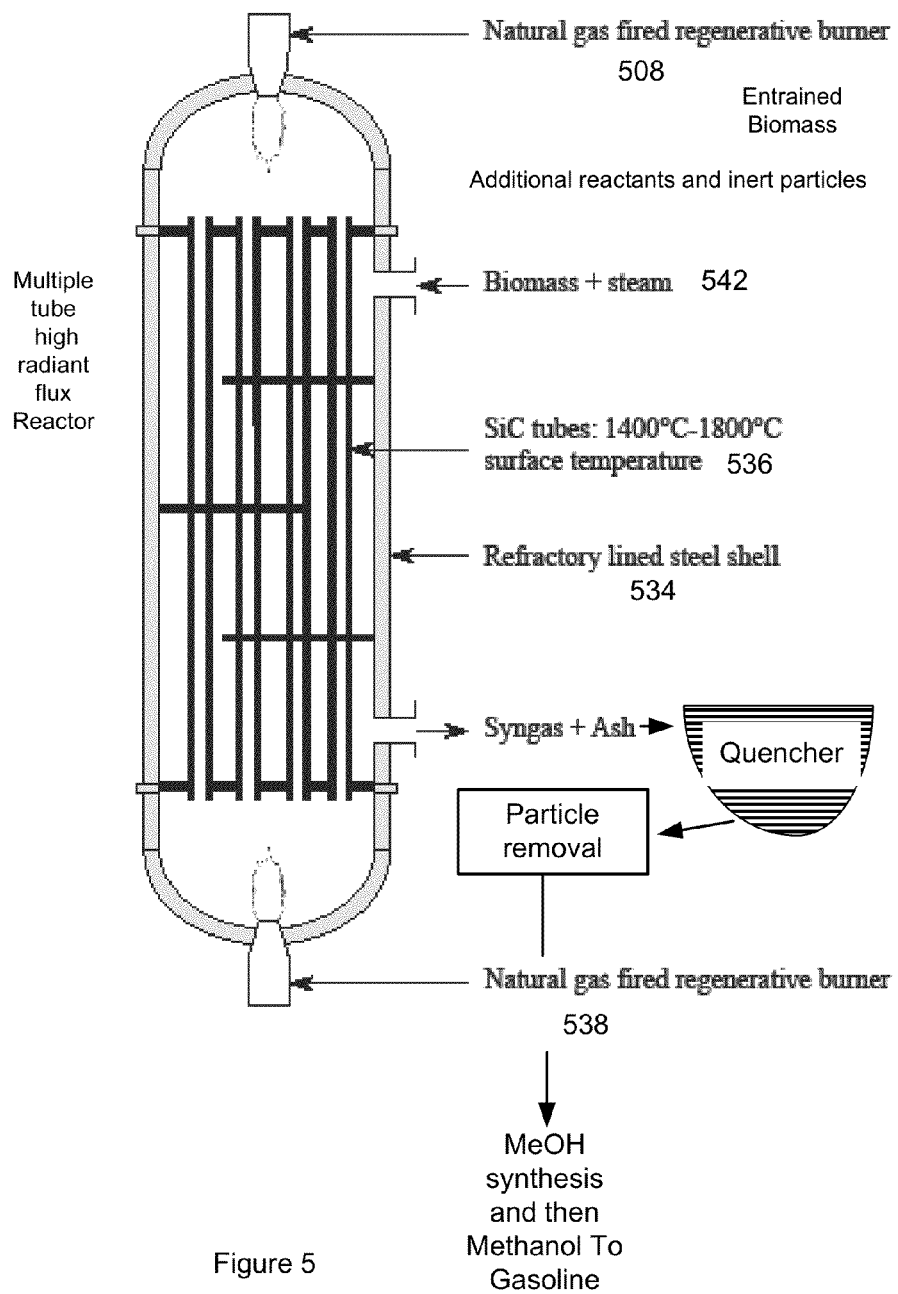
FIG. 5 illustrates a flow schematic of an embodiment for the radiant heat chemical reactor configured to generate chemical products including synthesis gas products.

FIG. 5 illustrates a flow schematic of an embodiment for the radiant heat chemical reactor configured to generate chemical products including synthesis gas products. The multiple shell radiant heat chemical reactor 514 includes a refractory vessel 534 having an annulus shaped cavity with an inner wall. The radiant heat chemical reactor 514 has two or more radiant tubes 536 made out of a solid material. The one or more radiant tubes 536 are located inside the cavity of the refractory lined vessel 534.

The exothermic heat source 538 heats a space inside the tubes 536. Thus, each radiant tube 536 is heated from the inside with an exothermic heat source 538, such as regenerative burners, at each end of the tube 536. Each radiant tube 536 is heated from the inside with fire and gases from the regenerative burners through heat insertion inlets at each end of the tube 536 and potentially by one or more heat insertion ports located in between the two ends. Flames and heated gas of one or more natural gas fired regenerative burners 538 act as the exothermic heat source supplied to the multiple radiant tubes at temperatures between 900° C. and 1800° C. and connect to both ends of the radiant tubes 536. Each tube 536 may be made of SiC or other similar material.

One or more feed lines 542 supply biomass and reactant gas into the top or upper portion of the chemical reactor 514. The feed lines 542 for the biomass particles and steam enter below the entry points in the refractory lined vessel 534 for the radiant tubes 536 that are internally heated. The feed lines 112 are configured to supply chemical reactants including 1) biomass particles, 2) reactant gas, 3) steam, 4) heat transfer aid particles, or 5) any of the four into the radiant heat chemical reactor. A chemical reaction driven by radiant heat occurs outside the multiple radiant tubes 536 with internal fires. The chemical reaction driven by radiant heat occurs within an inner wall of a cavity of the refractory lined vessel 534 and an outer wall of each of the one or more radiant tubes 536.

The chemical reaction may be an endothermic reaction including one or more of 1) biomass gasification ($C_nH_m + H_2O \rightarrow CO + H_2 + H_2O + X$), 2) and other similar hydrocarbon decomposition reactions, which are conducted in the radiant heat chemical reactor 514 using the radiant heat. A steam ($H_2O$) to carbon molar ratio is in the range of 1:1 to 1:4, and the temperature is high enough that the chemical reaction occurs without the presence of a catalyst.

The torrefied biomass particles used as a feed stock into the radiant heat reactor design conveys the beneficial effects of increasing and being able to sustain process gas temperatures of excess of 1200 degrees C. through more effective heat transfer of radiation to the particles entrained with the gas, increased gasifier yield of generation of syngas components of carbon monoxide and hydrogen for a given amount of biomass fed in, and improved process hygiene via decreased production of tars and C2+ olefins. The control system for the radiant heat reactor matches the radiant heat transferred from the surfaces of the reactor to a flow rate of the biomass particles to produce the above benefits.

The control system controls the gas-fired regenerative burners 538 to supply heat energy to the chemical reactor 514 to aid in causing the radiant heat driven chemical reactor to have a high heat flux. The inside surfaces of the chemical reactor 514 are aligned to 1) absorb and re-emit radiant energy, 2) highly reflect radiant energy, and 3) any combination of these, to maintain an operational temperature of the enclosed ultra-high heat flux chemical reactor 514. Thus, the inner wall of the cavity of the refractory vessel and the outer wall of each of the one or more tubes 536 emits radiant heat energy to, for example, the biomass particles and any other heat-transfer-aid particles present falling between an outside wall of a given tube 536 and an inner wall of the refractory vessel. The refractory vessel thus absorbs or reflects, via the tubes 536, the concentrated energy from the regenerative burners 538 positioned along on the top and bottom of the refractory vessel to cause energy transport by thermal radiation and reflection to generally convey that heat flux to the biomass particles, heat transfer aid particles and reactant gas inside the chemical reactor. The inner wall of the cavity of the thermal refractory vessel and the multiple tubes 536 act as radiation distributors by either absorbing radiation and re-radiating it to the heat-transfer-aid particles or reflecting the incident radiation to the heat-transfer-aid particles. The radiant heat chemical reactor 514 uses an ultra-high heat flux and high temperature that is driven primarily by radiative heat transfer, and not convection or conduction.

Convection biomass gasifiers used generally on coal particles typically at most reach heat fluxes of 5-10 kW/m^2. The high radiant heat flux biomass gasifier will use heat fluxes significantly greater, at least three times the amount, than those found in convection driven biomass gasifiers (i.e. greater than 25 kW/m^2). Generally, using radiation at high temperature (>950 degrees C. wall temperature), much higher fluxes (high heat fluxes greater than 80 kW/m^2) can be achieved with the properly designed reactor. In some instances, the high heat fluxes can be 100 kW/m^2-250 kW/m^2.

Next, the various algorithms and processes for the control system may be described in the general context of computer-executable instructions, such as program modules, being executed by a computer. Generally, program modules include routines, programs, objects, components, data structures, etc. that perform particular tasks or implement particular abstract data types. Those skilled in the art can implement the description and/or figures herein as computer-executable instructions, which can be embodied on any form of computer readable media discussed below. In general, the program modules may be implemented as software instructions, Logic blocks of electronic hardware, and a combination of both. The software portion may be stored on a machine-readable medium and written in any number of programming languages such as Java, C++, C, etc. The machine-readable medium may be a hard drive, external drive, DRAM, Tape Drives, memory sticks, etc. Therefore, the algorithms and controls systems may be fabricated exclusively of hardware logic, hardware logic interacting with software, or solely software.

While some specific embodiments of the invention have been shown the invention is not to be limited to these embodiments. For example, the recuperated waste heat from various plant processes can be used to pre-heat combustion air, or can be used for other similar heating means. Regenerative gas burners or conventional burners can be used as a heat source for the furnace. Alcohols C1, C2 and higher as well as ethers that are formed in the torrefaction process may be used as a high value in boosting the octane rating of the generated liquid fuel, such as gasoline. Biomass gasifier reactors other than a radiant heat chemical reactor may be used. The Steam Methane Reforming may be/include a SHR (steam hydrocarbon reformer) that cracks short-chained hydrocarbons (<C20) including hydrocarbons (alkanes, alkenes, alkynes, aromatics, furans, phenols, carboxylic acids, ketones, aldehydes, ethers, etc., as well as oxygenates into syngas components. The invention is to be understood as not limited by the specific embodiments described herein, but only by scope of the appended claims.

The invention claimed is:

1. An integrated plant to generate syngas from biomass, comprising:

a source of biomass;

a source of steam;

a steam explosion unit having an input cavity configured to receive the biomass as a feedstock from the source of biomass, two or more steam supply inputs configured to receive steam from the source of steam, and two or more stages operably coupled with each other, where a first and second stage each have at least one of the steam supply inputs, where the two or more stages are configured to pre-treat the biomass for subsequent supply to a biomass gasifier, where the stages are configured to use a combination of heat, pressure, and moisture that are applied to the biomass to make the biomass into a moist fine particle form, where the first stage of the steam explosion unit has a first steam supply input, where the first stage of the steam explosion unit is configured to use the combination of the heat, the pressure, and the moisture to break down a bulk structure of the received biomass, at least in part, by applying steam from the first steam supply input of the steam supply inputs to begin degrading bonds between lignin and hemi-cellulose from cellulose fibers of the biomass and increase a moisture content of the received biomass, and where the second stage of the steam explosion unit has a second steam supply input, where the second stage of the steam explosion unit is configured to apply steam at at least ten times atmospheric pressure from the second steam supply input of the steam supply inputs to heat and pressurize any gases and fluids present inside the biomass to internally blow apart the bulk structure of the received biomass via a rapid depressurization of the biomass with the increased moisture content and the degraded bonds, where the first and second stages cooperate with one another to produce, from the biomass, the moist fine particle form having average dimensions of less than 70 microns thick and less than 500 microns in length, and those produced moist fine particles of biomass are adapted for subsequent feeding to a feed section of the biomass gasifier operably coupled downstream from the stages; and where the biomass gasifier has a reactor vessel configured to react the biomass in moist fine particle form with a decreased particle size due to being blown apart by the steam explosion unit, where the biomass gasifier has a third steam supply input and one or more heat sources, and in the reactor vessel, in the presence of the steam from the third steam supply input and heat from the heat sources, the biomass in fine particle form is adapted to react in a rapid biomass gasification reaction to produce at least syngas components, including hydrogen (H2) and carbon monoxide (CO), where the steam explosion unit and the biomass gasifier are part of the integrated plant.

2. The integrated plant of claim 1, where the two or more stages of the steam explosion unit include a thermally hydrating stage and a steam explosion stage, where the thermally hydrating stage has the input cavity configured to receive chips of the biomass and the first steam supply input to apply low pressure saturated steam into a vessel containing the chips of biomass at an elevated temperature of above 60 degrees C. but less than 145 degrees C. at a pressure around atmospheric PSI, to start a decomposition, hydrating, and softening of the received biomass in chip form, where the chips of biomass stay in the thermally hydrating stage long enough to saturate with moisture.

3. The integrated plant of claim 2, where the thermally hydrating stage is configured to feed the chips of biomass that have been softened and increased in moisture content to the steam explosion stage, which is at a pressure 10 to 40 times the pressure as is present in the thermally hydrating stage, and the steam explosion stage is configured to further raise the moisture content of biomass to at least 40% by weight and preferably 50 to 60% moisture content by weight, where a weight of water is divided by a total weight consisting of the chips of biomass plus the weight of the water.

4. The integrated plant of claim 1, where after the thermally hydrating stage, another of the two or more stages is configured to any combination of 1) crushed and 2) compressed the softened biomass in chip form into a plug form, which is then fed into a continuous screw conveyor system which moves the biomass in the plug form into the steam explosion stage, where in the continuous screw conveyor system, the biomass in the plug form prevents blow back backpressure from high pressure steam present in the steam explosion stage from affecting the thermally hydrating stage, and an outlet of the biomass gasifier configured to supply reaction products from the biomass gasifier to a downstream organic liquid product synthesis reactor, where the steam explosion unit, the biomass gasifier, and the downstream organic liquid product synthesis reactor are part of the integrated plant; and the biomass in the moist fine particle form allows a more thorough reaction of the biomass making the reaction products better suited for the downstream organic liquid product synthesis reactor.

5. The integrated plant of claim 2, where the steam explosion stage is configured to expose the biomass to high temperature and high pressure steam at at least 188 degrees C. and 160 PSI from the second steam input for at least 5 minutes and preferably around 10 minutes until moisture penetrates porous portions of the bulk structure of the biomass and all of the fluids and gases in the biomass are raised to the high pressure, where the conveyor system is configured to feed the biomass through the steam explosion stage to an exit, where a small opening goes into a tube that is maintained at reduced pressure and any internal fluids or gases at the high pressure expand to internally blow apart the bulk structure of the biomass into the moist fine particles of biomass.

6. The integrated plant of claim 1, where the two or more stages of the steam explosion unit include a thermally hydrating stage and a steam explosion stage, where the thermally hydrating stage has the steam applied to the biomass at a temperature above a glass transition point of the lignin in order to soften and elevate the moisture content of the biomass so that at least the cellulose fibers of the biomass in the steam explosion stage can be internally blown apart from the biomass, where the thermally hydrating stage is configured to receive the biomass in chip form which could include leaves, needles, bark, and wood, and then the chips of biomass are heated to greater than 60° C. using the steam, and in the steam explosion stage, the softened and hydrated chips of biomass are exposed to high temperature and high pressure steam for a set time period to create high pressure steam inside the partially hollow cellulose fibers and other porous areas in the bulk structure of the biomass material, and then the pressure at an exit in the steam explosion stage is dropped rapidly by extruding the bulk structure of the biomass at between 160 to 850 PSI into a tube at reduced pressure to cause an internal explosion, which internally blows apart the biomass into minute fine particles of biomass, where internally blowing apart the bulk structure of biomass in a fiber bundle into pieces and fragments of the cellulose fiber, the lignin and the hemi-cellulose results in both 1) an increase of a surface area of the biomass in fine particle form compared to the received biomass in chip form, and 2) a change in structure of the resulting produced biomass in the fine particle form to flow like grains of sand rather than like fibers.

7. The integrated plant of claim 1, where the two or more stages of the steam explosion unit include a thermally hydrating stage and a steam explosion stage, and an exit of the steam explosion stage couples to a blow line, where the blow line at the exit of the steam explosion stage is configured to allow steam flashing when once the biomass explodes into the moist fine particle form, then the produced particles of biomass lose a percentage of the moisture content due to the steam flashing in the blow line and are vented off as a water vapour through a vent, a cyclone filter configured to separate the produced particles of biomass and moisture from the blow line by the cyclone filter, a dryer configured to reduce the moisture content of the fine particles of biomass, where the moisture content of the fine particles of biomass is further dried out by the dryer to reduce the moisture content of the fine particles of biomass to 1-20% by weight preferably and up to 30% in general, where the dryer is configured to then feed the fine particles of biomass with their reduced moisture content to the biomass gasifier.

8. The integrated plant of claim 1, where the produced fine particles of biomass with reduced moisture content includes the cellulose fibers that are fragmented, torn, shredded, and any combination of these, and have an average dimension of less than 30 microns thick and less than 200 microns in length;

another stage of the two or more stages configured to feed the produced fine particles of biomass with the average dimension of less than 30 microns thick and less than 200 microns in length downstream to the biomass gasifier for the rapid biomass gasification reaction in the reactor vessel of the biomass gasifier so that they create a higher surface to volume ratio for the same amount of biomass compared to the received biomass in chip form, which allows a higher heat and mass transfer to the biomass material and a more rapid thermal decomposition and gasification of all the molecules in the biomass in the rapid biomass gasification reaction in the reactor vessel.

9. The integrated plant of claim 2, where the steam explosion stage of the steam explosion unit is configured to be filled with high pressure steam, contains a discharge outlet configured to "explode" the biomass material to a next stage at reduced pressure to produce the biomass in fine particle form, where the biomass in fine particle form flows through a feed line of a blow vessel at high velocity, and flow aids, including any of 1) flowable solids and 2) gases are injected at any of 1) the discharge outlet of the steam explosion stage and 2) in the feed line to prevent clogs by the biomass, and in addition the feed line has heating coils traced around the feed line to maintain an elevated temperature of the biomass in fine particle form to help prevent crystallization of rosins and resin acids in the biomass in fine particle form.

10. The integrated plant of claim 1, further comprising:
a water separation unit configured to receive the biomass reduced into smaller particle sizes and in pulp from a collection chamber at an outlet stage of the steam explosion stage and then remove water from the biomass in fine particle form in a cyclone unit, where the reduced moisture content of less than 20% by weight of the biomass in fine particle form is fed by a conveying system to a torrefaction unit to undergo torrefaction, drying, or pyrolyzation of the biomass at a temperature of less than 700 degrees C. for a preset amount of time.

11. An integrated plant to produce biomass in fine particle form, comprising:
a source of biomass;
a source of steam;
a steam explosion unit having an input cavity configured to receive the biomass as a feedstock from the source of biomass,
two or more steam supply inputs configured to receive steam from the source of steam,
two or more stages operably coupled with each other and configured to pre-treat the biomass for subsequent supply to a densification unit,
i) where the stages are configured to use a combination of heat, pressure, and moisture that are applied to the biomass to make the biomass into a moist fine particle form,
ii) where a first stage of the steam explosion unit has a first steam supply input, where the first stage of the steam explosion unit is configured to break down a bulk structure of the received biomass, at least in part, by applying steam from the first steam supply input of the steam supply inputs to begin degrading bonds between lignin and hemi-cellulose from cellulose fibers of the biomass and increase a moisture content of the received biomass, and
iii) where a second stage of the steam explosion unit has a second steam supply input, where the second stage of the steam explosion unit is configured to apply steam at at least ten times atmospheric pressure from the second steam supply input of the steam supply inputs in order to heat and pressurize any gases and fluids present inside the biomass to internally blow apart the bulk structure of the biomass via a rapid depressurization of the biomass with the increased moisture content and the degraded bonds,
where the first and second stages cooperate with one another to produce, from the biomass, the moist fine particle form having average dimensions of less than 50 microns thick and less than 500 microns in length, and those produced moist fine particles of biomass are adapted for subsequent feeding, in slurry form, from an output of the steam explosion unit directly to the densification unit, where the densification unit, which is operably coupled with the stages, is configured to densify the biomass in moist particle form into denser forms, including but not limited to pellets of biomass, and
where the biomass, in densified form, is adapted for subsequent feeding into one or more of 1) a biomass gasifier operably coupled downstream from the stages and configured to react the biomass in the presence of steam from the steam source and heat from the heat source, 2) a combustion unit for processing heat, 3) a combustion unit to generate electric power, 4) a process unit to produce chemicals, and 5) a packaging unit for storage or transport to applications where biomass pellets are utilized, each of which is operably coupled with the densification unit.

12. The integrated plant of claim 11, further comprising a dryer that is configured to dry moisture content of the biomass received in moist particle form from the steam explosion unit to between 0% and 45% before the dried biomass is sent to the densification unit.

* * * * *